US005856128A

United States Patent [19]
Bandman et al.

[11] Patent Number: 5,856,128
[45] Date of Patent: Jan. 5, 1999

[54] HUMAN NUCLEIC ACID BINDING PROTEIN

[75] Inventors: Olga Bandman, Mountain View; Janice Au-Young, Berkeley; Phillip R. Hawkins, Mountain View; Jennifer L. Hillman, San Jose, all of Calif.

[73] Assignee: Incyte Pharmaceuticals, Inc., Palo Alto, Calif.

[21] Appl. No.: 698,407

[22] Filed: Aug. 15, 1996

[51] Int. Cl.[6] .................................................. C12N 15/00
[52] U.S. Cl. .................. 435/69.1; 435/320.1; 435/252.3; 435/252.33; 536/23.1; 536/23.5; 530/350; 530/358
[58] Field of Search ................... 536/23.1, 23.5; 435/252.3, 252.33, 69.1, 320.1; 530/350, 358

[56] References Cited

PUBLICATIONS

Hu et al. (1996) GenBank Database, Accession No. U51586.
Fisher, D.E., et al., "Pulse labeling of small nuclear ribonucleoproteins in vivo reveals distinct patterns of antigen recognition by human autoimmune antibodies", *Proc. Natl. Acad. Sci.*, 81: 31855–3189 (1984).
Hermann, H., et al., "snRNP Sm proteins share two evolutionarily conserved sequence motifs which are involved in Sm protein–protein interactions", *EMBO J.*, 14:2076–2088 (1995).
Kanaar, R., et al., "The Conserved Pre–mRNA Splicing Factor U2AF from Drosophila: Requirement for Viability", *Science*, 262:569–573 (1993).
Koren, E., "Murine and Human Antibodies to Native DNA That Cross–React with the A and D SnRNP Polypeptides Cause Direct Injury of Cultured Kidney Cells", *J. Immunol.*, 154:4857–4864 (1995).
Lee, C.G., et al., "RNA Annealing Activity Is Intrinsically Associated with U2AF", *J. Biol. Chem.*, 268:13472–13478 (1993).

Pang, Q., et al., "Two cDNAs from the plant *Arabidopsis thaliana* that partially restore recombination proficiency and DNA–damage resistance to *E. coli* mutants lacking recombination–intermediate–resolution activities", *Nuc. Acids Res.*, 21:1647–1653 (1993).
Tsukahara, T., et al., "Regulation of alternative splicing in the amyloid precursor protein (APP) mRNA during neuronal and glial differentiation of P19 embryonal carcinoma cells" *Brain Res.*, 679:178–183 (1995).
Zamore, P.D., et al., "Cloning and domain structure of the mammalian splicing factor U2AF", *Nature*, 355:609–614 (1992).
Hu, Y. et al., (GI 1809248) GenBank Sequence Database (Accession U51586) National Center for Biotechnology Information: National Library of Medicine, Bethesda, Maryland 20894 (Direct Submission) (1996).

*Primary Examiner*—Robert A. Wax
*Assistant Examiner*—Enrique D. Longton
*Attorney, Agent, or Firm*—Lucy J. Billings; Incyte Pharmaceuticals, Inc.

[57] ABSTRACT

The present invention provides polynucleotides which identify and encode a novel human nucleic acid binding protein (NABP). The invention provides for genetically engineered expression vectors and host cells comprising the nucleic acid sequences encoding NABP. The invention also provides for the use of substantially purified NABP or its antagonists, in pharmaceutical compositions for the treatment of diseases associated with the expression of NABP. Additionally, the invention provides for the use of antisense molecules to NABP in pharmaceutical compositions for treatment of diseases associated with the expression of NABP. The invention also describes diagnostic assays which utilize diagnostic compositions comprising the polynucleotide, fragments or the complement thereof, which hybridize with the genomic sequence or the transcript of polynucleotides encoding NABP or anti-NABP antibodies which specifically bind to NABP.

6 Claims, 7 Drawing Sheets

FIGURE 1A

```
                    9              18              27              36              45           54
5' CAT CAC TTA CCA CTA GTT TTA CAT CGT GAC TGG TGC AAA CCC TAG GCT GTT
                    63              72              81              90              99         108
   ACC CAC ACG TTA AGT CGC CGT TTC AGC ACA TTA GTT GCC GGA GCA GCG GTG CTG
                    117            126             135             144            153         162
   GGT ACC CTG GGC ACA CCT GGA CTG ACA GCA TCC CCA GCA CTG GCC CAG CCC
                    171            180             189             198            207         216
   CTG GGC ACT TTG CCC CAG GCT GTC ATG GCT GTC CAG CCT GGA GTC ATC ACA
                                               M   A   V   Q   P   G   V   I   T
                    225            234             243             252            261         270
   GGT GTG ACC CCA GCC CGT CGT CCT CCT ATC CCG GTC ACC GTG TCG GTG GTG
    G   V   T   P   A   R   R   P   P   I   P   V   T   V   S   V   V
                    279            288             297             306            315         324
   GTG AAC CCC ATC CTG GCC AGC CCT CCA ACG CTG GGT CTC CTG GAG CCC AAG AAG
    V   N   P   I   L   A   S   P   P   T   L   G   L   L   E   P   K   K
                    333            342             351             360            369         378
   GAG AAG GAA GAG GAG CTG TTT CCC CCA GAG TCA GAG CGG CCA CAC GAG ATG CTG AGC
    E   K   E   E   E   L   F   P   P   E   S   E   R   P   H   E   M   L   S
                    387            396             405             414            423         432
   GAG CAG GAG CAC ATG AGC AGC GGC AGT AGC GCC CGA GCC ATG GTG ATG CAG
    E   Q   E   H   M   S   S   G   S   S   A   R   A   M   V   M   Q
                    441            450             459             468            477         486
   AAG CTG CTC CGC AAG CAG GAG TCT ACA GTG ATG GTT CTG CGC AAC ATG GTG GAC
    K   L   L   R   K   Q   E   S   T   V   M   V   L   R   N   M   V   D
                    495            504             513             522            531         540
   CCC AAG GAC ATC GAT GAT GAC CTG GAA GGG GAG GTG ACA GAG GAG TGT GGC AAG
    P   K   D   I   D   D   D   L   E   G   E   V   T   E   E   C   G   K
```

FIGURE 1A

```
TTC GGG GCC GTG AAC CGC GTC ATC TAC CAA GAG AAA CAA GGC GAG GAG GAG
 F   G   A   V   N   R   V   I   Y   Q   E   K   Q   G   E   E   E
549         558         567         576         585         594

GAT GCA GAA ATC ATT GTC AAG ATC TTT GTG GAG TTT TCC ATA GCC TCT GAG ACT
 D   A   E   I   I   V   K   I   F   V   E   F   S   I   A   S   E   T
603         612         621         630         639         648         702

CAT AAG GCC ATC CAG GCC CTC AAT GGC CGC TGG TTT GCT GGC AAG TGG TGG
 H   K   A   I   Q   A   L   N   G   R   W   F   A   G   K   W   W
657         666         675         684         693         702

CTG AAG TGT ACG ACC AGG AGC GTT TTG ATA ACA GTG ACC TCT CTG CGT GAC AGT
 L   K   C   T   T   R   S   V   L   I   T   V   T   S   L   R   D   S
711         720         729         738         747         756         810

GGT CCC TCT CCC CGG ACT TGC ACT TGT TCC TTG TTT CCT CTG GGT TTT ATA GTG
 G   P   S   P   R   T   C   T   C   S   L   F   P   L   G   F   I   V
765         774         783         792         801         810         864

ATA CAG TGG TGT CCC CGG GGC CAG GCG CGC TCT GCC CAG CCC AGC CTA CAG TGC
 I   Q   W   C   P   R   G   Q   A   R   S   A   Q   P   S   L   Q   C
819         828         837         846         855         864

GGA TAA AGG TGC TGC GGA TGC TGC CCC TG 3'
 G   *
873         882         891
```

FIGURE 1B

```
Confidential -- Property of Incyte Pharmaceuticals, Inc.
LIFESEQ Version 4.1AUG96

The Electronic Northern for Clone: 609036
and Stringency >= 50

Library     Lib Description                                        Abun    Pct Abun
---------   -----------------------------------------------------   ----    --------
OVARTUM01   ovarian tumor, 36 F, NORM, WM                            1       0.2695
HIPONOT01   brain, hippocampus, 72 F                                 1       0.0535
MYOMNOT01   uterus, myometrium, 43 F                                 1       0.0409
CARDNOT01   heart, 65 M                                              1       0.0398
PROSTUT03   prostate tumor, 67 M, match to PROSNOT05                 1       0.0352
PANCNOT04   pancreas, 5 M                                            2       0.0338
OVARTUT01   ovarian tumor, 43 F, match to OVARNOT03                  1       0.0323
FIBRSEM01   fibroblasts, senescent, NORM, WM                         1       0.0312
PROSTUT05   prostate tumor, 69 M, match to PROSNOT07                 1       0.0303
COLNTUT06   large intestine, cecal tumor, 45 F                       1       0.0293
LUNGNOT09   lung, fetal M                                            1       0.0286
LUNGNOT10   lung, fetal M                                            1       0.0261
STOMFET01   stomach, fetal F                                         1       0.0255
MMLR1DT01   macrophages (adher PBMNC), M/F, 24-hr MLR                1       0.0236
KERANOT01   keratinocytes, neonatal M                                1       0.0228
COLNNOT01   colon, 75 M, match to COLNTUT02                          1       0.0213
SCORNOT01   spinal cord, 71 M                                        1       0.0201
MMLR2DT01   macrophages (adher PBMNC), M/F, 48-hr MLR                1       0.0177
BRAITUT02   brain tumor, metastasis, 58 M                            1       0.0169
PLACNOT02   placenta, fetal F                                        1       0.0168
KIDNNOT05   kidney, neonatal F                                       1       0.0161
PGANNOT01   paraganglia, 46 M                                        1       0.0160
BRSTNOT02   breast, 55 F, match to BRSTTUT01                         1       0.0158
BRSTNOT05   breast, 58 F, match to BRSTTUT03                         1       0.0154
BRSTTUT01   breast tumor, 55 F, match to BRSTNOT02                   1       0.0151
LUNGAST01   lung, asthma, 17 M                                       1       0.0150
BRAITUT01   brain tumor, oligoastrocytoma, 50 F                      1       0.0134
LIVSFEM02   liver/spleen, fetal M, NORM, WM                          3       0.0080

Electronic Northern Results returned a total of 28 row(s).
```

FIGURE 2

```
1   M- - - - - - - - - - - - - A A Q A P - - - - - - - - - - -   SEQ ID NO-1
1   M L G G L Y G D L P P P T D D E K P S - - - - - - - - - - -   SEQ ID NO-3
1   M - - S D F D E F E R Q L N E N K Q E R D K E N R H R K R S   SEQ ID NO-4
1   M - - G - Y D D - - - - - - - - - R E R D R E R R R H - - -   SEQ ID NO-5

7   - - - - - - - - - - - - - G V I T G V - - - - - - - - - - -   SEQ ID NO-1
20  - - - - - - - - - - - - - G N S S V W S R S T K M A P P T L   SEQ ID NO-3
29  H S R S R S R D R K R R S R S R D R R N R D Q R S A S R D R   SEQ ID NO-4
16  - - R S R S R D R - H R E R S R D R R H H - - - - - - R N S   SEQ ID NO-5

13  - - T P A - - - - - - - - - - - - - R P I P V T I P S V       SEQ ID NO-1
38  R K P P A - - - - - - - - - - - - - F A P P Q T I L R P L     SEQ ID NO-3
59  R R R S K P L T R G A K E E H G G L I R S P R H E K K K K V   SEQ ID NO-4
37  R R K P - - - - - - - - - - - - - - - - - - - - - - - - -     SEQ ID NO-5

27  - - - - G V V N P - - - - I L A S P - - - - - - - - - - - -   SEQ ID NO-1
54  - - - - N K P K P - - - - I V S A P Y K P - - - - - - - P P   SEQ ID NO-3
89  R K Y W D V P P P G F E H I T P M Q Y K A M Q A A G Q I P A   SEQ ID NO-4
41  S L Y W D V P P P G F E H I T P M Q Y K A M Q A S G Q I P A   SEQ ID NO-5

37  - P T L G L L E P - - - - - - - - - - - - - - - - - - - -     SEQ ID NO-1
69  N S S Q S V L I P A N E S A P S H Q P A L V G - - V T S S V   SEQ ID NO-3
119 T A L L P T M T P D G L A V T P T P V P V V G S Q M T R Q A   SEQ ID NO-4
71  S - - - - - V V P D T - - - P Q T A V P V V G S T I T R Q A   SEQ ID NO-5

45  - - - - - - - - - - - - - - - - - - - - - - - K K - - - -     SEQ ID NO-1
97  I E E Y D P A R P N D Y E E - - - - - - Y K R E K K - - - -   SEQ ID NO-3
149 R R L Y V G N I P F G I T E E A M M D F F N A Q M R L G G L   SEQ ID NO-4
93  R R L Y V G N I P F G V T E E M M E F F N Q Q M H L V G L     SEQ ID NO-5

47  - E K E E E - - - - - - - - - - - - - - E L - - - - - - -     SEQ ID NO-1
117 - R K A T E A E M K R E M D K R R Q V - - - - - - - - - -     SEQ ID NO-3
179 T Q A P G N P V L A V Q I N Q D K N F A F L E F R S V D E T   SEQ ID NO-4
123 A Q A A G S P V L A C Q I N L D K N F A F L E F R S I D E T   SEQ ID NO-5

54  - - - - - F P E S E R P E - - - - - - - - - - - - - - - -     SEQ ID NO-1
135 - - - - - - Y P E R D M R E R E E R E R R E R E I T V I L S V SEQ ID NO-3
209 T Q A M A F D G I I F Q G Q S L K I R R P H D Y Q P L P G M   SEQ ID NO-4
153 T Q A M A F D G I N L K G Q S L K I R R P H D Y Q P M P G I   SEQ ID NO-5

62  - - - - - - - - - - - - - - - - - - M L S E Q E H M S I S G   SEQ ID NO-1
160 - D I S G E E R G R D P A R V V V E V L G R E D P R L L P G   SEQ ID NO-3
239 S E - - - - N P S V Y V P G V V S T V V P D S A H K L F I G   SEQ ID NO-4
183 T D T P A I K P A V V S S G V I S T V V P D S P H K I F I G   SEQ ID NO-5

74  S - - - - - - - - - - - - - - - - - - - - - - - - - - - -     SEQ ID NO-1
189 N V D G F - - - - - - - - - - - - S I G K S K P S G L G V G A SEQ ID NO-3
265 G L P N Y L N D D Q V K E L L T S F G P L K A F N L V K D S   SEQ ID NO-4
213 G L P N Y L N D D Q V K E L L L S F G K L R A F N L V K D A   SEQ ID NO-5
```

FIGURE 3A

```
 75  - - - - S A R - - - - H M V M Q K L L R K Q E - - - - - - -    SEQ ID NO-1
208  G G Q M T P A - - - - Q R M M P K M G W K Q G Q G L G K S E    SEQ ID NO-3
295  A T G L S K G Y A F C E Y V D I N V T D Q A I A G L N G M Q    SEQ ID NO-4
243  A T G L S K G Y A F C E Y V D L S I T D Q S I A G L N G M Q    SEQ ID NO-5

90  - - - - - - - - - - - - - - - - - - - - - - - - - - - - -    SEQ ID NO-1
234  Q G I P T P L M A K K T - - D R R A G V I V N A S E N K S S    SEQ ID NO-3
325  L G D K K L L V Q R A S V G A K N A T L V S P P S T I N Q T    SEQ ID NO-4
273  L G D K K L I V Q R A S V G A K N A - - - - Q N A A N T T Q    SEQ ID NO-5

90  - - - - - - - - - - - - - - - - - S T V M V L R N M V          SEQ ID NO-1
262  S A E K K V V - - - - K S V N I N G E P T R V L L R N M V      SEQ ID NO-3
355  P V T L Q V P G L M S S Q V Q M G G H P T E V L C M N M V      SEQ ID NO-4
299  S V M L Q V P G L - - S N V V T S G P P T E V L C L N M V      SEQ ID NO-5

100  D P K D I D D L E - - - - - G E V T E E C G K F G A V N R      SEQ ID NO-1
288  G P G Q V D D E L E - - - - - D E V G G E C A K Y G T V T R    SEQ ID NO-3
385  L P E E L L D D E E Y E E I V E D V R D E C S K Y G L V K S    SEQ ID NO-4
327  T P D E L R D E E E Y E D I L E D I K E E C T K Y G V V R S    SEQ ID NO-5

125  V I I Y Q E K Q G E E E D A E I I V K I F V E F S I A S E T    SEQ ID NO-1
313  V L I F E I T E P N F P V H E A V - R I F V Q F S R P E E T    SEQ ID NO-3
415  I E I - - P R P V D G V E V P G C G K I F V E F T S V F D C    SEQ ID NO-4
357  V E I - - P R P I E G V E V P G C G K V F V E F N S V L D C    SEQ ID NO-5

155  H K A I Q A L N G R W F A G R K W W L K C T T R S V L I T V    SEQ ID NO-1
342  T K A L V D L D G R Y F G G R - - - - - - T V R A T F Y D E    SEQ ID NO-3
443  Q K A M Q G L T G R K F A N R - - - - - - V V V T K Y C D P    SEQ ID NO-4
385  Q K A Q Q A L T G R K F S D R - - - - - - V V V T S Y F D P    SEQ ID NO-5

185  T S L R D S G P S P R T C T C S L F P L G F I V I Q W C P R    SEQ ID NO-1
366  E K F S K N E L A P V - - - - - - - - - - - - - - - - - -      SEQ ID NO-3
467  D S Y H R R D - - - - - - - - - - - F - - - - - - - - W        SEQ ID NO-4
409  D K Y H R R E - - - - - - - - - - - F                          SEQ ID NO-5

215  G Q A R S A Q P S L Q C G                                      SEQ ID NO-1
377  - - - - - - - P G E I P G                                      SEQ ID NO-3
475                                                                 SEQ ID NO-4
416                                                                 SEQ ID NO-5
```

Decoration 'Decoration #1': Box residues that match the Consensus

FIGURE 3B

HUMAN NUCLEIC ACID BINDING PROTEIN

FIELD OF THE INVENTION

The present invention relates to nucleic acid and amino acid sequences of a novel human nucleic acid binding protein and to the use of these sequences in the diagnosis, study, prevention and treatment of disease.

BACKGROUND OF THE INVENTION

DNA recombination, DNA repair, and RNA splicing are multistep processes that rely on protein complexes (Coleman J E et al (1980) CRC Crit Rev Biochem 7: 247–289). These complexes may bind, unwind, anneal, cleave, and otherwise modify DNA or RNA. Typically, several protein subunits contribute to these complexes.

In a search for molecules that enable plants to resist the DNA damaging effects of ultraviolet radiation, researchers discovered the *Arabidopsis thaliana* Drt111 protein (Pang Q et al (1993) Nuc Acids Res 21: 1647–1653). Drt111 partially restores recombination proficiency and DNA-damage resistance to *E. coli* ruvC mutants, cleaving single-stranded DNA in homologous recombination intermediates (Holliday junctions).

Nucleic acid binding and modifying proteins are also required for splicing pre-mRNA in the cell nucleus. One such protein is the U2 snRNP auxiliary factor (U2AF) which has been shown to bind pre-mRNA (Zamore P et al (1992) Nature 355: 609–614). U2AF belongs to a family of splicing factor genes that possess multiple repeats of the RS dipeptide at either their N or C terminus. The RS domain has been shown to be essential for annealing complementary RNA or DNA sequences and for binding RNA (Lee C G et al (1993) J Biol Chem 268: 13472–13478).

Nucleic Acid Binding Proteins and Disease

One of the hallmarks of Alzheimer's disease is the deposition of a processed form of amyloid precursor protein (APP) outside of brain cells (Soto C et al (1994) J Neurochem 63: 1191–1198). As P19 EC cells differentiate into glial cells, expression of U2AF is reduced and APP is alternatively spliced Transfection with U2AF restores the original APP splice variant, thus U2AF is believed to play a critical role in glial-specific splicing of APP (Tsukahara T et al (1995) Brain Res 679: 178–183).

Auto-antibodies against snRNPs were found to be common in systemic lupus erythematosus (SLE) and related autoimmune disorders (Fisher D E et al (1984) Proc Natl Acad Sci 81: 3185–3189). Later, auto-antibodies to U2 snRNP and the other snRNPs were found to be diagnostic for SLE (Hermann H et al EMBO J 14: 2076–2088). In cell culture experiments, Koren et al (1995, J Immunol 154: 4857–4864) found that antibodies derived from a murine model for SLE were pathogenic only when they had reactivity with snRNP components. Thus, an autoimmune response to snRNP components appears to be important in SLE pathology.

More than a million Americans suffer from dementia, a permanent and often progressive decline in intellectual function that substantially interferes with a person's social and economic activity. Alzheimer's disease is a major cause of dementia and its prevalence is growing. Currently, there are no known treaments that stop or reverse the relentless progression in the impairment in mental abilities of Alzheimer's disease patients. Similarly, there are no known treatments that permanently end SLE. Current treatments for SLE control the inflammatory responses that are a consequence of SLE, but do not mask the antigen that promotes the production of self-reactive immune cells. Thus, a new nucleic acid binding protein would satisfy this need in the art by providing new agents for the diagnosis and treatment of Alzheimer's disease and various autoimmune disorders such as SLE.

SUMMARY

The present invention discloses a novel human nucleic acid binding protein (hereinafter referred to as NABP), characterized as having homology to *Arabidopsis thaliana* Drt111 (GI 166694) and human and Drosophila U2 snRNP auxiliary factor large subunits (GI 267188 and GI 627165, respectively). Accordingly, the invention features a substantially purified nucleic acid binding protein, as shown in amino acid sequence of SEQ ID NO:1, and having characteristics of nucleic acid binding proteins.

One aspect of the invention features isolated and substantially purified polynucleotides which encode NABP. In a particular aspect, the polynucleotide is the nucleotide sequence of SEQ ID NO:2. In addition, the invention features polynucleotide sequences that hybridize under stringent conditions to SEQ ID NO:2.

The invention further relates to nucleic acid sequences encoding NABP, oligonucleotides, peptide nucleic acids (PNA), fragments, portions or antisense molecules thereof, and expression vectors and host cells comprising polynucleotides which encode NABP. The present invention also relates to antibodies which bind specifically to NABP, pharmaceutical compositions comprising substantially purified NABP, fragments thereof, or antagonists of NABP, in conjunction with a suitable pharmaceutical carrier, and methods for producing NABP, fragments thereof, or antagonists of NABP.

BRIEF DESCRIPTION OF THE FIGURES

FIGS. 1A and 1B show the amino acid sequence (SEQ ID NO:1) and nucleic acid sequence (SEQ ID NO:2) of the novel nucleic acid binding protein, NABP. The alignment was produced using MacDNAsis software (Hitachi Software Engineering Co Ltd, San Bruno, Calif.).

FIG. 2 shows the northern analysis for Incyte Clone 609036. The northern analysis was produced electronically using LIFESEQ database (Incyte Pharmaceuticals, Palo Alto Calif.).

FIGS. 3A and 3B show the amino acid sequence alignments among NABP (SEQ ID NO:1), A thaliana Drt111 (GI 166694; SEQ ID NO:3), human U2 snRNP auxiliary factor large subunit (GI 267188; SEQ ID NO:4), and Drosophila snRNP auxiliary factor large subunit (GI 627165; SEQ ID NO:5) produced using the multisequence alignment program of DNAStar software (DNAStar Inc, Madison Wis.).

DETAILED DESCRIPTION OF THE INVENTION

Definitions

Figure 4:
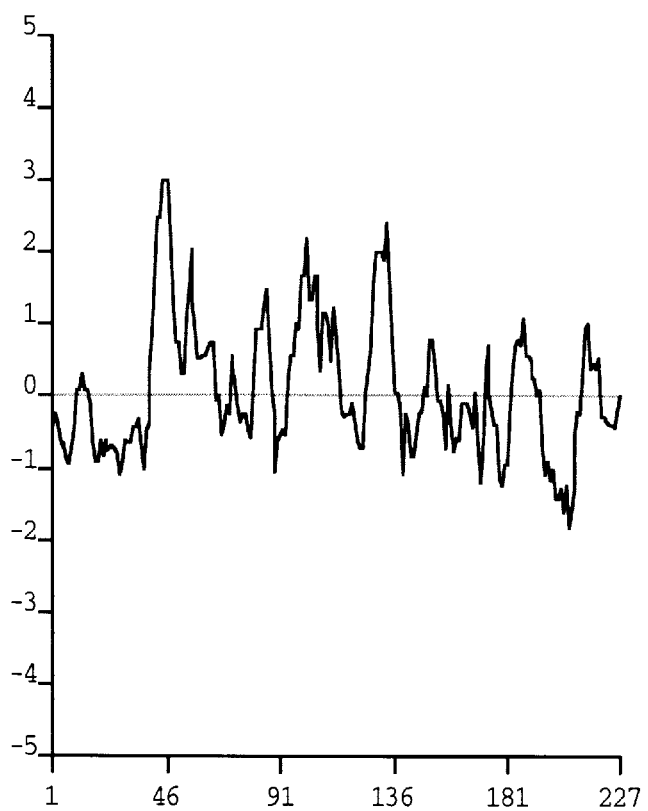
FIG. 4 shows the hydrophobicity plot (generated using MacDNAsis software) for NABP, SEQ ID NO:1; the X axis reflects amino acid position, and the negative Y axis, hydrophobicity (FIGS. 4 and 5).

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to peptide or protein sequence. "Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen P E et al (1993) Anticancer Drug Des 8:53–63).

As used herein, NABP refers to the amino acid sequences of substantially purified NABP obtained from any species, particularly mammalian, including bovine, ovine, porcine, murine, equine, and preferably human, from any source whether natural, synthetic, semi-synthetic or recombinant.

A "variant" of NABP is defined as an amino acid sequence that is altered by one or more amino acids. The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNAStar software.

A "deletion" is defined as a change in either amino acid or nucleotide sequence in which one or more amino acid or nucleotide residues, respectively, are absent.

An "insertion" or "addition" is that change in an amino acid or nucleotide sequence which has resulted in the addition of one or more amino acid or nucleotide residues, respectively, as compared to the naturally occurring NABP.

A "substitution" results from the replacement of one or more amino acids or nucleotides by different amino acids or nucleotides, respectively.

The term "biologically active" refers to a NABP having structural, regulatory or biochemical functions of a naturally occurring NABP. Likewise, "immunologically active" defines the capability of the natural, recombinant or synthetic NABP, or any oligopeptide thereof, to induce a specific immune response in appropriate animals or cells and to bind with specific antibodies.

The term "derivative" as used herein refers to the chemical modification of a nucleic acid encoding NABP or the encoded NABP. Illustrative of such modifications would be replacement of hydrogen by an alkyl, acyl, or amino group. A nucleic acid derivative would encode a polypeptide which retains essential biological characteristics of natural NABP.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated. "Stringency" typically occurs in a range from about Tm-5° C. (5° C. below the Tm of the probe)to about 20° C. to 25° C. below Tm. As will be understood by those of skill in the art, a stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs J (1994) Dictionary of Biotechnology, Stockton Press, New York N.Y.). Amplification as carried out in the polymerase chain reaction technologies is described in Dieffenbach C W and G S Dveksler (1995, PCR Primer, a Laboratory Manual, Cold Spring Harbor Press, Plainview N.Y.).

Preferred Embodiments

The present invention relates to a novel human nucleic acid binding protein and to the use of the nucleic acid and amino acid sequences in the study, diagnosis, prevention and treatment of disease. cDNAs encoding a portion of NABP were found in cDNA libraries from a variety of tissues including many types of tumors (FIG. 2).

The present invention also encompasses NABP variants. A preferred NABP variant is one having at least 80% amino acid sequence similarity to the NABP amino acid sequence (SEQ ID NO:1), a more preferred NABP variant is one having at least 90% amino acid sequence similarity to SEQ ID NO:1 and a most preferred NABP variant is one having at least 95% amino acid sequence similarity to SEQ ID NO:1.

Nucleic acids encoding the human nucleic acid binding protein of the present invention were first identified in cDNA, Incyte Clones 609036 (SEQ ID NO:2) from the colon tissue library, COLNNOT01, through a computer-generated search for amino acid sequence alignments. The following Incyte clones (and cDNA libraries from which they were derived) were extended and assembled to create the consensus sequence (SEQ ID NO:2): 60936 (COLNNOT01); 242897 (HIPONOT01); 284323 (CARDNOT01); 454485 (KERANOT01); 518848 (MMLR1DT01); 523888 (MMLR2DT01); 554053 (SCORNOT01), 603191 (BRSTN2T1), 618337 (PGANNOT01); 758021 (BRAITUT02); 779444 (MYOMNOT01); 789689 (PROSTUT3); 817073 (OVARTUT01); 841557 (PROSTUT05); 868692 (LUNGAST01); 958268 (KIDNNOT05); 969065 (BRSTN5T3); 978194 (BRSTN2T1); 1355140 (LUNGNOT09); 1375382 (LUNGNOT10); 1231587 (BRAITUT01); and 1303488 (PLACNOT02). The nucleic acid sequence of SEQ ID NO:2 encodes the NABP amino acid sequence, SEQ ID NO:1.

Figure 5:
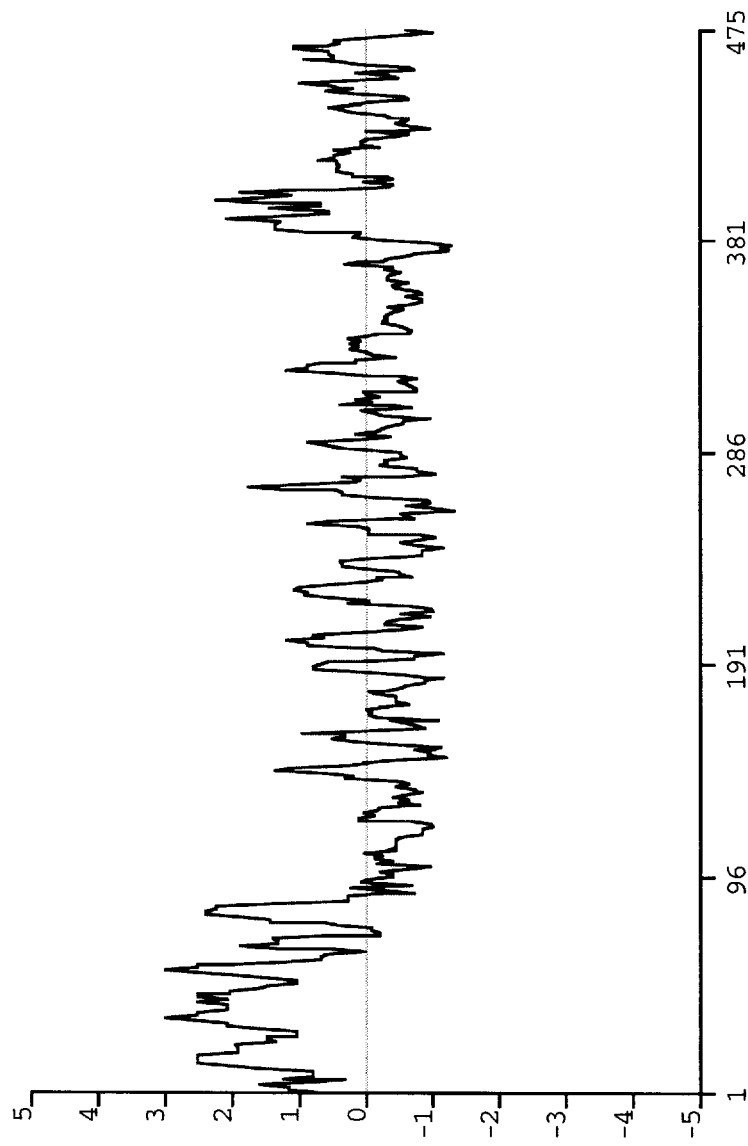
FIG. 5 shows the hydrophobicity plot for human U2 snRNP auxiliary factor large subunit, SEQ ID NO:4.

The present invention is based, in part, on the chemical and structural homology among NABP, A. thaliana Drt111 (GI 166694; Pang et al, supra), the human U2 snRNP auxiliary factor large subunit (GI 267188; Zamore et al, supra), and the Drosophila U2 snRNP auxiliary factor large subunit (GI 627165; Kanaar R et al (1993) Science 262: 569–573; FIGS. 3A and 3B). The novel NABP is 227 amino acids long and shares 29% identity with Drt111, and 21% identity, with human U2 snRNP auxiliary factor large subunit. NABP has 2 RS amino acid repeats near its C terminus (FIGS. 1A and 1B). As illustrated by FIGS. 4 and 5, NABP and the carboxy-terminal region of the human U2 snRNP auxiliary factor large subunit have similar hydrophobicity plots suggesting similar structure.

The NABP Coding Sequences

The nucleic acid and deduced amino acid sequences of NABP are shown in FIGS. 1A and 1B. In accordance with the invention, any nucleic acid sequence which encodes the amino acid sequence of NABP can be used to generate recombinant molecules which express NABP. In a specific embodiment described herein, a nucleotide sequence encoding a portion of NABP was first isolated as Incyte Clone 609036 from a colon tissue cDNA library (COLNNOT01).

It will be appreciated by those skilled in the art that as a result of the degeneracy of the genetic code, a multitude of NABP-encoding nucleotide sequences, some bearing minimal homology to the nucleotide sequences of any known and naturally occurring gene may be produced. The invention contemplates each and every possible variation of nucleotide sequence that could be made by selecting combinations based on possible codon choices. These combinations are made in accordance with the standard triplet genetic code as applied to the nucleotide sequence of naturally occurring NABP, and all such variations are to be considered as being specifically disclosed.

Although nucleotide sequences which encode NABP and its variants are preferably capable of hybridizing to the nucleotide sequence of the naturally occurring NABP under appropriately selected conditions of stringency, it may be advantageous to produce nucleotide sequences encoding NABP or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding NABP and its derivatives without altering the encoded amino acid sequences include the production of RNA transcripts having more desirable properties, such as a greater half-life, than transcripts produced from the naturally occurring sequence.

It is now possible to produce a DNA sequence, or portions thereof, encoding NABP and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a sequence encoding NABP or any portion thereof.

Also included within the scope of the present invention are polynucleotide sequences that are capable of hybridizing to the nucleotide sequences of FIGS. 1A and 1B under various conditions of stringency. Hybridization conditions are based on the melting temperature (Tm) of the nucleic acid binding complex or probe, as taught in Berger and Kimmel (1987, *Guide to Molecular Cloning Techniques, Methods in Enzymology*, Vol 152, Academic Press, San Diego Calif.) incorporated herein by reference, and confer may be used at a defined stringency.

Altered nucleic acid sequences encoding NABP which may be used in accordance with the invention include deletions, insertions or substitutions of different nucleotides resulting in a polynucleotide that encodes the same or a functionally equivalent NABP. The protein may also show deletions, insertions or substitutions of amino acid residues which produce a silent change and result in a functionally equivalent NABP. Deliberate amino acid substitutions may be made on the basis of similarity in polarity, charge, solubility, hydrophobicity, hydrophilicity, and/or the amphipathic nature of the residues as long as the biological activity of NABP is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of NABP. As used herein, an "allele" or "allelic sequence" is an alternative form of NABP. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, SEQUENASE® (U.S. Biochemical Corp, Cleveland Ohio)), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the Hamilton Micro Lab 2200 (Hamilton, Reno Nev.), Peltier Thermal Cycler (PTC200; M J Research, Watertown Mass.) and the ABI 377 DNA sequencers (Perkin Elmer).

Extending the Polynucleotide Sequence

The polynucleotide sequence encoding NABP may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO® 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequences is that of Parker J D et al (1991; Nucleic Acids Res 19:3055–60). Additionally, one can use PCR, nested primers and PromoterFinder libraries to walk in genomic DNA (PROMOTER FINDER™ Clontech (Palo Alto Calif.). This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze the size or confirm the nucleotide sequence of sequencing or PCR products. Systems for rapid sequencing are available from Perkin Elmer, Beckman Instruments (Fullerton Calif.), and other companies. Capillary sequencing may employ flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eg. GENOTYPER™ and SEQUENCE NAVIGATOR™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez MC et al (1993) Anal Chem 65:2851–2858).

Expression of the Nucleotide Sequence

In accordance with the present invention, polynucleotide sequences which encode NABP, fragments of the polypeptide, fusion proteins or functional equivalents thereof may be used in recombinant DNA molecules that direct the expression of NABP in appropriate host cells. Due to the inherent degeneracy of the genetic code, other DNA sequences which encode substantially the same or a functionally equivalent amino acid sequence, may be used to clone and express NABP. As will be understood by those of skill in the art, it may be advantageous to produce NABP-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of NABP expression or to produce recombinant RNA transcripts having desirable properties, such as a longer half-life, than transcripts produced from naturally occurring sequence.

The nucleotide sequences of the present invention can be engineered in order to alter an NABP coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant polynucleotides encoding NABP may be ligated to a heterologous sequence to encode a fusion protein. For example, for screening of peptide libraries for inhibitors of NABP activity, it may be useful to encode a chimeric NABP protein that is recognized by a commercially available antibody. A fusion protein may also be engineered to contain a cleavage site located between an NABP sequence and the heterologous protein sequence, so that the NABP may be cleaved and purified away from the heterologous moiety.

In an alternate embodiment of the invention, the coding sequence of NABP may be synthesized, whole or in part, using chemical methods well known in the art (see Caruthers M H et al (1980) Nuc Acids Res Symp Ser 215–23, Horn T et al(1980) Nuc Acids Res Symp Ser 225–32, etc). Alternatively, the protein itself could be produced using chemical methods to synthesize an NABP amino acid sequence, whole or in part. For example, peptide synthesis can be performed using various solid-phase techniques (Roberge J Y et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be substantially by preparative high performance liquid chromatography (eg, Creighton (1983) *Proteins, Structures and Molecular Principles,* W H Freeman and Co, New York N.Y.). The composition of the synthetic peptides may be confirmed by amino acid analysis or sequencing (eg, the Edman degradation procedure; Creighton, supra). Additionally the amino acid sequence of NABP, or any part thereof, may be altered during direct synthesis and/or combined using chemical methods with sequences from other proteins, or any part thereof, to produce a variant polypeptide.

Expression Systems

In order to express a biologically active NABP, the nucleotide sequence encoding NABP or its functional equivalent, is inserted into an appropriate expression vector, ie, a vector which contains the necessary elements for the transcription and translation of the inserted coding sequence.

Methods which are well known to those skilled in the art can be used to construct expression vectors containing an NABP coding sequence and appropriate transcriptional or translational controls. These methods include in vitro recombinant DNA techniques, synthetic techniques and in vivo recombination or genetic recombination. Such techniques are described in Sambrook et al (1989) *Molecular Cloning, A Laboratory Manual,* Cold Spring Harbor Press, Plainview N.Y. and Ausubel F M et al (1989) *Current Protocols in Molecular Biology,* John Wiley & Sons, New York N.Y.

A variety of expression vector/host systems may be utilized to contain and express an NABP coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the BLUE-SCRIPT® phagemid (Stratagene, LaJolla Calif.) or pSport1 (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of NABP, vectors based on SV40 or EBV may be used with an appropriate selectable marker.

In bacterial systems, a number of expression vectors may be selected depending upon the use intended for NABP. For example, when large quantities of NABP are needed for the induction of antibodies, vectors which direct high level expression of fusion proteins that are readily purified may be desirable. Such vectors include, but are not limited to, the multifunctional E. coli cloning and expression vectors such as BLUESCRIPT® (Stratagene), in which the NABP coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding NABP may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi R M (1991) Results Probl Cell Differ 17:85–105) may be used. These constructs can be introduced into plant cells by direct DNA transformation or pathogen-mediated transfection. For reviews of such techniques, see Hobbs S or Murry L E in McGraw Hill Yearbook of Science and Technology (1992) McGraw Hill New York N.Y., pp 191–196 or Weissbach and Weissbach (1988) Methods for Plant Molecular Biology, Academic Press, New York N.Y., pp 421–463.

An alternative expression system which could be used to express NABP is an insect system. In one such system, Autography californica nuclear polyhedrosis virus (AcNPV) is used as a vector to express foreign genes in Spodoptera fruaiperda cells or in Trichoplusia larvae. The NABP coding sequence may be cloned into a nonessential region of the virus, such as the polyhedrin gene, and placed under control of the polyhedrin promoter. Successful insertion of NABP will render the polyhedrin gene inactive and produce recombinant virus lacking coat protein coat. The recombinant viruses are then used to infect S. frugiperda cells or Trichoplusia larvae in which NABP is expressed (Smith et al (1983) J Virol 46:584; Engelhard EK et al (1994) Proc Nat Acad Sci 91:3224–7).

In mammalian host cells, a number of viral-based expression systems may be utilized. In cases where an adenovirus is used as an expression vector, an NABP coding sequence may be ligated into an adenovirus transcription/translation complex consisting of the late promoter and tripartite leader sequence. Insertion in a nonessential E1 or E3 region of the viral genome will result in a viable virus capable of expressing NABP in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of an NABP sequence. These signals include the ATG initiation codon and adjacent sequences. In cases where NABP, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express NABP may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk- or aprt- cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S C and R C Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes Calif. et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the NABP is inserted within a marker gene sequence, recombinant cells containing NABP can be identified by the absence of marker gene function. Alternatively, a marker gene can be placed in tandem with a NABP sequence under the control of a single promoter. Expression of the marker gene in response to induction or selection usually indicates expression of the tandem NABP as well.

Alternatively, host cells which contain the coding sequence for NABP and express NABP may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the polynucleotide sequence encoding NABP can be detected by DNA-DNA or DNA-RNA hybridization or amplification using probes, portions or fragments of polynucleotides encoding NABP. Nucleic acid amplification based assays involve the use of oligonucleotides or oligomers based on the NABP-encoding sequence to detect transformants containing DNA or RNA encoding NABP. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of NABP, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on NABP is preferred, but a competitive binding assay may be employed. These and other assays are described, among other places, in Hampton R et al (1990, Serological Methods, a Laboratory Manual, APS Press, St Paul Minn.) and Maddox D E et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to polynucleotides encoding NABP include oligolabeling, nick translation, end-labeling or PCR amplification using a labeled nucleotide. Alternatively, the NABP sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 incorporated herein by reference.

Purification of NABP

Host cells transformed with a nucleotide sequence encoding NABP may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing polynucleotides encoding NABP can be designed with signal sequences which direct secretion of NABP through a prokaryotic or eukaryotic cell membrane. Other recombinant constructions may join NABP to nucleotide sequence encoding a polypeptide domain which will facilitate purification of soluble proteins (Kroll D J et al (1993) DNA Cell Biol 12:441–53; of discussion of vectors infra containing fusion proteins).

NABP may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and NABP is useful to facilitate purification. One such expression vector provides for expression of a fusion protein compromising an NABP and contains nucleic acid encoding 6 histidine residues followed by thioredoxin and an enterokinase cleavage site. The histidine residues facilitate purification on IMIAC (immobilized metal ion affinity chromotography as described in Porath et al (1992) Protein Expression and Purification 3: 263–281) while the enterokinase cleavage site provides a means for purifying NABP from the fusion protein.

In addition to recombinant production, fragments of NABP may be produced by direct peptide synthesis using solid-phase techniques (cf Stewart et al (1969) Solid-Phase Peptide Synthesis, W H Freeman Co, San Francisco; Merrifield J (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of NABP may be chemically synthesized separately and combined using chemical methods to produce the full length molecule.

Uses of NABP

The rationale for use of the nucleotide and polypeptide sequences disclosed herein is based in part on the chemical and structural homology among the novel NABP disclosed herein, A. thaliana Drt111 (GI 166–694; Pang et al, supra), human U2 snRNP auxilliary factor large subunit (GI 267188; Zamore et al, supra), and Drosophila U2 snRNP auxilliary factor large subunit (GI 627165; Kanaar et al, supra).

Accordingly, NABP or an NABP derivative may be used to treat Alzheimer's disease and autoimmune disorders, such as SLE. In those conditions where NABP activity is not desirable, cells could be transfected with antisense sequences of NABP-encoding polynucleotides or provided with antagonists of NABP.

NABP Antibodies

NABP-specific antibodies are useful for the diagnosis of conditions and diseases associated with expression of NABP. Such antibodies may include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

NABP for antibody induction does not require biological activity; however, the protein fragment, or oligopeptide must be antigenic. Peptides used to induce specific antibodies may have an amino acid sequence consisting of at least five amino acids, preferably at least 10 amino acids. Preferably, they should mimic a portion of the amino acid sequence of the natural protein and may contain the entire amino acid sequence of a small, naturally occurring molecule. Short stretches of NABP amino acids may be fused with those of another protein such as keyhole limpet hemocyanin and antibody produced against the chimeric molecule. Procedures well known in the art can be used for the production of antibodies to NABP.

For the production of antibodies, various hosts including goats, rabbits, rats, mice, etc may be immunized by injection with NABP or any portion, fragment or oligopeptide which retains immunogenic properties. Depending on the host species, various adjuvants may be used to increase immunological response. Such adjuvants include but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to NABP may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce NABP-specific single chain antibodies Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for NABP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse W D et al (1989) Science 256:1275–1281).

A variety of protocols for competitive binding or immunoradiometric assays using either polyclonal or monoclonal antibodies with established specificities are well known in the art. Such immunoassays typically involve the formation of complexes between NABP and its specific antibody and the measurement of complex formation. A two-site, monoclonal-based immunoassay utilizing monoclonal antibodies reactive to two noninterfering epitopes on a specific NABP protein is preferred, but a competitive binding assay may also be employed. These assays are described in Maddox D E et al (1983, J Exp Med 158:1211).

Diagnostic Assays using NABP Specific Antibodies

Particular NABP antibodies are useful for the diagnosis of conditions or diseases characterized by expression of NABP or in assays to monitor patients being treated with NABP, agonists or inhibitors. Diagnostic assays for NABP include methods utilizing the antibody and a label to detect NABP in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring NABP, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on NABP is preferred, but a competitive binding assay may be employed. These assays are described, among other places, in Maddox, Del. et al (1983, J Exp Med 158:1211).

In order to provide a basis for diagnosis, normal or standard values for NABP expression must be established. This is accomplished by combining body fluids or cell extracts taken from normal subjects, either animal or human, with antibody to NABP under conditions suitable for complex formation which are well known in the art. The amount of standard complex formation may be quantified by comparing various artificial membranes containing known quantities of NABP with both control and disease samples from biopsied tissues. Then, standard values obtained from normal samples may be compared with values obtained from samples from subjects potentially affected by disease. Deviation between standard and subject values establishes the presence of disease state.

Drug Screening

NABP, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between NABP and the agent being tested, may be measured.

Another technique for drug screening which may be used provides for high throughput screening of compounds having suitable binding affinity to the NABP is described in detail in "Determination of Amino Acid Sequence Antigenicity" by Geysen H N, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of NABP and washed. Bound NABP is then detected by methods well known in the art. Purified NABP can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding NABP specifically compete with a test compound for binding NABP. In this manner, the antibodies can be used to detect the presence of any peptide which shares one or more antigenic determinants with NABP.

Uses of the Polynucleotide Encoding NABP

A polynucleotide encoding NABP, or any part thereof, may be used for diagnostic and/or therapeutic purposes. For diagnostic purposes, polynucleotides encoding NABP of this invention may be used to detect and quantitate gene expression in biopsied tissues in which expression of NABP may be implicated. The diagnostic assay is useful to distinguish between absence, presence, and excess expression of NABP and to monitor regulation of NABP levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding NABP or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring sequences encoding NABP, alleles or related sequences.

Probes may also be used for the detection of related sequences and should preferably contain at least 50% of the nucleotides from any of these NABP encoding sequences. The hybridization probes of the subject invention may be derived from the nucleotide sequence of SEQ ID NO:2 or from genomic sequence including promoter, enhancer elements and introns of the naturally occurring NABP. Hybridization probes may be labeled by a variety of reporter groups, including radionuclides such as 32P or 35S, or enzymatic labels such as alkaline phosphatase coupled to the probe via avidin/biotin coupling systems, and the like.

Other means for producing specific hybridization probes for DNAs encoding NABP include the cloning of nucleic acid sequences encoding NABP or NABP derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Polynucleotide sequences encoding NABP may be used for the diagnosis of conditions or diseases with which the expression of NABP is associated. For example, polynucleotide sequences encoding NABP may be used in hybridization or PCR assays of fluids or tissues from biopsies to detect NABP expression. The form of such qualitative or quantitative methods may include Southern or northern analysis, dot blot or other membrane-based technologies; PCR technologies; dip stick, pIN, chip and ELISA technologies. All of these techniques are well known in the art and are the basis of many commercially available diagnostic kits.

The nucleotide sequences encoding NABP disclosed herein provide the basis for assays that detect activation or induction associated with Alzheimer's disease and autoimmune disorders, such as SLE. The nucleotide sequence encoding NABP may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of nucleotide sequences encoding NABP in the sample indicates the presence of the associated disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for NABP expression must be established. This is accomplished by combining body fluids or cell extracts taken from normal subjects, either animal or human, with NABP, or a portion thereof, under conditions suitable for hybridization or amplification. Standard hybridization may be quantified by comparing the values obtained for normal subjects with a dilution series of NABP run in the same experiment where a known amount of a substantially purified NABP is used. Standard values obtained from normal samples may be compared with values obtained from samples from patients afflicted with NABP-associated diseases. Deviation between standard and subject values is used to establish the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR, as described in U.S. Pat. Nos. 4,683,195 and 4,965,188, provides additional uses for oligonucleotides based upon the NABP sequence. Such oligomers are generally chemically synthesized, but they may be generated enzymatically or produced from a recombinant source. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. For example, the presence of a relatively high amount of NABP in extracts of biopsied tissues may indicate the onset of SLE. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutic Use

Based upon its homology to genes encoding Drt111 and U2AP, and its expression profile, polynucleotide sequences encoding NABP disclosed herein may be useful in the treatment of conditions such as Alzheimer's disease and autoimmune disorders, such as SLE.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense polynucleotides of the gene encoding NABP. See, for example, the techniques described in Sambrook et al (supra) and Ausubel et al (supra).

The polynucleotides comprising full length cDNA sequence and/or its regulatory elements enable researchers to use sequences encoding NABP as an investigative tool in sense (Youssoufian H and H F Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding NABP can be turned off by transfecting a cell or tissue with expression vectors which express high levels of a desired NABP-encoding fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of gene encoding NABP, ie, the promoters, enhancers, and introns. Oligonucleotides derived from the transcription initiation site, eg, between –10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J E et al (In: Huber B E and B I Carr (1994) *Molecular and Immunologic Approaches,* Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of sequences encoding NABP.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding NABP. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient as presented in U.S. Pat. Nos. 5,399,493 and 5,437,994, disclosed herein by reference. Delivery by transfection and by liposome are quite well known in the art.

Furthermore, the nucleotide sequences for NABP disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for NABP can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price CM (1993; Blood Rev 7:127–34) and Trask B J (1991; Trends Genet 7:149–54).

The technique of fluorescent in situ hybridization of chromosome spreads has been described, among other places, in Verma et al (1988) *Human Chromosomes: A Manual of Basic Techniques,* Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of the gene encoding NABP on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers may be used for extending genetic maps. For example a sequence tagged site based map of the human genome was recently published by the Whitehead-MIT Center for Genomic Research (Hudson T J et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that is known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of NABP, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

It is contemplated, for example, that NABP or an NABP derivative can be delivered in a suitable formulation to block the progression of Alzheimer's disease and autoimmune disorders, such as SLE. Similarly, administration of NABP antagonists may also inhibit the activity or shorten the lifespan of this protein.

The examples below are provided to illustrate the subject invention and are not included for the purpose of limiting the invention.

EXAMPLES

I cDNA Library Construction

The COLNNOT01 cDNA library was constructed from tissue removed from the normal colon of a 75 year old male. The frozen tissue was immediately homogenized and lysed using a Brinkmann Homogenizer Polytron PT-3000 (Brinkmann Instruments Inc, Westbury N.Y.) in guanidinium isothiocyanate buffer. Lysates were then loaded on a 5.7M CsCl cushion and ultracentrifuged in a SW28 swinging bucket rotor for 18 hours at 25,000 rpm at ambient temperature. The RNA was extracted once with acid phenol and precipitated using 0.3M sodium acetate and 2.5 volumes of ethanol, resuspended in DEPC-treated water and DNase treated for 25 min at 37° C. The reaction was stopped with an equal volume of acid phenol, and the RNA was isolated using the Qiagen Oligotex kit (QIAGEN Inc, Chatsworth Calif.) and used to construct the CDNA library.

The RNA was handled according to the recommended protocols in the SuperScript Plasmid System for cDNA Synthesis and Plasmid Cloning (catalog #18248-013; Gibco/

BRL). cDNAs were fractionated on a Sepharose CL4B column (catalog #275105, Pharmacia), and those cDNAs exceeding 400 bp were ligated into pSport I. The plasmid pSport I was subsequently transformed into DH5a$^a$ competent cells (Cat. #18258-012, Gibco/BRL).

II Isolation and Sequencing of cDNA Clones

Plasmid DNA was released from the cells and purified using the Miniprep Kit (Catalogue # 77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Catalog # 22711, LIFE TECHNOLOGIES$^a$, Gaithersburg Md.) with carbenicillin at 25 mg/L and glycerol at 0.4%; 2) the bacteria were cultured for 24 hours after the wells were inoculated and then lysed with 60 μl of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

The cDNAs were sequenced by the method of Sanger F and A R Coulson (1975; J Mol Biol 94:441f), using a Hamilton Micro Lab 2200 (Hamilton, Reno Nev.) in combination with four Peltier Thermal Cyclers (PTC200 from M J Research, Watertown Mass.) and Applied Biosystems 377 or 373 DNA Sequencing Systems (Perkin Elmer), and reading frame was determined.

III Homology Searching of CDNA Clones and Their Deduced Proteins

Each cDNA was compared to sequences in GenBank using a search algorithm developed by Applied Biosystems and incorporated into the INHERIT 670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S F (1993) J Mol Evol 36:290–300; Altschul, S F et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labelled nucleotide sequence to a membrane on which RNAs from a particular cell type or tissue have been bound (Sambrook et al. supra).

Analogous computer techniques using BLAST (Altschul S F 1993 and 1990, supra) are used to search for identical or related molecules in nucleotide databases such as GenBank or the LIFESEQ™ database (Incyte, Palo Alto Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into acccount both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

V Extension of NABP-Encoding Polynucleotides to Full Length or to Recover Regulatory Elements Full length NABP-encoding nucleic acid sequence (SEQ ID NO:2) is used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers allow the extension of the known NABP-encoding sequence "outward" generating amplicons containing new, unknown nucleotide sequence for the region of interest (U.S. patent application Ser. No. 08/487,112, filed Jun. 7, 1995, specifically incorporated by reference). The initial primers are designed from the cDNA using OLIGO 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M J Research, Watertown Mass.) and the following parameters:

| Step 1  | 94° C. for 1 min (initial denaturation)  |
|---------|-------------------------------------------|
| Step 2  | 65° C. for 1 min                          |
| Step 3  | 68° C. for 6 min                          |
| Step 4  | 94° C. for 15 sec                         |
| Step 5  | 65° C. for 1 min                          |
| Step 6  | 68° C. for 7 min                          |
| Step 7  | Repeat step 4–6 for 15 additional cycles  |
| Step 8  | 94° C. for 15 sec                         |
| Step 9  | 65° C. for 1 min                          |
| Step 10 | 68° C. for 7:15 min                       |
| Step 11 | Repeat step 8–10 for 12 cycles            |
| Step 12 | 72° C. for 8 min                          |
| Step 13 | 4° C. (and holding)                       |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQUICK™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent *E. coli* cells (in 40 μl of appropriate media) are transformed with 3 μl of ligation mixture and cultured in 80 μl of SOC medium (Sambrook J et al, supra). After incubation for one hour at 37° C., the whole transformation mixture is plated on Luria Bertani (LB)-agar (Sambrook J et al, supra) containing 2×Carb. The following day, several colonies are randomly picked from each plate and cultured in 150 μl of liquid LB/2×Carb medium placed in an individual well of an appropriate, commercially-available, sterile 96-well microtiter plate. The following day, 5 μl of each overnight culture is transferred into a nonsterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer and one or both of the gene specific primers used for the extension reaction are added to each well. Amplification is performed using the following conditions:

| Step 1 | 94° C. for 60 sec |
|--------|--------------------|
| Step 2 | 94° C. for 20 sec |
| Step 3 | 55° C. for 30 sec |
| Step 4 | 72° C. for 90 sec |

-continued

| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of [$\gamma$-$^{32}$P] adenosine triphosphate (Amersham, Chicago Ill.) and T4 polynucleotide kinase (DuPont NEN®, Boston Mass.). The labeled oligonucleotides are substantially purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT ARm film (Kodak, Rochester N.Y.) is exposed to the blots in a Phosphoimager cassette (Molecular Dynamics, Sunnyvale Calif.) for several hours, hybridization patterns are compared visually.

VII Antisense Molecules

The NABP-encoding sequence, or any part thereof, is used to inhibit in vivo or in vitro expression of naturally occurring NABP. Although use of antisense oligonucleotides, comprising about 20 base-pairs, is specifically described, essentially the same procedure is used with larger cDNA fragments. An oligonucleotide based on the coding sequences of NABP, as shown in FIGS. 1A and 1B is used to inhibit expression of naturally occurring NABP. The complementary oligonucleotide is designed from the most unique 5' sequence as shown in FIGS. 1A and 1B and used either to inhibit transcription by preventing promoter binding to the upstream nontranslated sequence or translation of an NABP-encoding transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIGS. 1A and 1B.

VIII Expression of NABP

Expression of the NABP is accomplished by subcloning the cDNAs into appropriate vectors and transfecting the vectors into host cells. In this case, the cloning vector, pSport, previously used for the generation of the cDNA library is used to express NABP in *E. coli*. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length NABP-encoding sequence. The signal sequence directs the secretion of NABP into the bacterial growth media which can be used directly in the following assay for activity.

IX NABP Activity

NABP binding to RNA or DNA can be assessed by a method described by Zamore et al (1992, supra). $^{32}$P-labelled RNA or DNA and NABP are incubated 1 hour at 25° C. with 20 U RNasin (for RNA only), 1 mg/ml yeast tRNA in 50 mM KCl, 10 mM HEPES-KOH (pH 8.0), 0.025% Nonidet P-40, 1 mM dithiothreitol, and 10% glycerol. DNA-protein or RNA-protein complexes are then analyzed by electrophoresis on polyacrylamide gels.

X Production of NABP Specific Antibodies

NABP substantially purified using PAGE electrophoresis (Sambrook, supra) is used to immunize rabbits and to produce antibodies using standard protocols. The amino acid sequence translated from NABP is analyzed using DNAStar software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions (shown in FIG. 4) is described by Ausubel FM et al (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel FM et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring NABP Using Specific Antibodies

Naturally occurring or recombinant NABP is substantially purified by immunoaffinity chromatography using antibodies specific for NABP. An immunoaffinity column is constructed by covalently coupling NABP antibody to an activated chromatographic resin such as CnBr-activated Sepharose (Pharmacia Biotech). After the coupling, the resin is blocked and washed according to the manufacturer's instructions.

Media containing NABP is passed over the immunoaffinity column, and the column is washed under conditions that allow the preferential absorbance of NABP (eg, high ionic strength buffers in the presence of detergent). The column is eluted under conditions that disrupt antibody/NABP binding (eg, a buffer of pH 2–3 or a high concentration of a chaotrope such as urea or thiocyanate ion), and NABP is collected.

XII Identification of Molecules Which Interact with NABP

NABP, or biologically active fragments thereof, are labelled with $^{125}$I Bolton-Hunter reagent (Bolton, A E and Hunter, W M (1973) Biochem J 133: 529). Candidate molecules previously arrayed in the wells of a 96 well plate are incubated with the labelled NABP, washed and any wells with labelled NABP complex are assayed. Data obtained using different concentrations of NABP are used to calculate values for the number, affinity, and association of NABP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. An isolated and purified polynucleotide sequence encoding the protein having the amino acid sequence of SEQ ID NO: 1.

2. The polynucleotide sequence of claim 1 consisting of the polynucleotide sequence of SEQ ID NO:2.

3. An isolated and purified polynucleotide sequence which is the complement SEQ ID NO:2.

4. An expression vector containing the polynucleotide sequence of claim 1.

5. A host cell comprising the polynucleotide sequence of claim 1.

6. A method for producing a polypeptide comprising the amino acid of SEQ ID NO:1, the method comprising the steps of:
   a) culturing the host cell of claim 5 under conditions suitable for the expression of the polypeptide; and
   b) recovering the polypeptide from the host cell culture.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 227 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:

(A) LIBRARY:
(B) CLONE: Consensus (xi) SEQUENCE DESCRIPTION: SEQ ID NO:1:

| Met | Ala | Ala | Gln | Ala | Pro | Gly | Val | Ile | Thr | Gly | Val | Thr | Pro | Ala | Arg |
|---|---|---|---|---|---|---|---|---|---|---|---|---|---|---|---|
| 1 | | | | 5 | | | | | 10 | | | | | 15 | |

| Pro | Pro | Ile | Pro | Val | Thr | Ile | Pro | Ser | Val | Gly | Val | Val | Asn | Pro | Ile |
|---|---|---|---|---|---|---|---|---|---|---|---|---|---|---|---|
| | | | 20 | | | | | 25 | | | | | 30 | | |

| Leu | Ala | Ser | Pro | Pro | Thr | Leu | Gly | Leu | Leu | Glu | Pro | Lys | Lys | Glu | Lys |
|---|---|---|---|---|---|---|---|---|---|---|---|---|---|---|---|
| | | 35 | | | | | 40 | | | | | 45 | | | |

| Glu | Glu | Glu | Glu | Leu | Phe | Pro | Glu | Ser | Glu | Arg | Pro | Glu | Met | Leu | Ser |
|---|---|---|---|---|---|---|---|---|---|---|---|---|---|---|---|
| | 50 | | | | | 55 | | | | | 60 | | | | |

| Glu | Gln | Glu | His | Met | Ser | Ile | Ser | Gly | Ser | Ser | Ala | Arg | His | Met | Val |
|---|---|---|---|---|---|---|---|---|---|---|---|---|---|---|---|
| 65 | | | | | 70 | | | | | 75 | | | | | 80 |

| Met | Gln | Lys | Leu | Leu | Arg | Lys | Gln | Glu | Ser | Thr | Val | Met | Val | Leu | Arg |
|---|---|---|---|---|---|---|---|---|---|---|---|---|---|---|---|
| | | | | 85 | | | | | 90 | | | | | 95 | |

| Asn | Met | Val | Asp | Pro | Lys | Asp | Ile | Asp | Asp | Leu | Glu | Gly | Glu | Val |
|---|---|---|---|---|---|---|---|---|---|---|---|---|---|---|
| | | | 100 | | | | 105 | | | | | 110 | | |

| Thr | Glu | Glu | Cys | Gly | Lys | Phe | Gly | Ala | Val | Asn | Arg | Val | Ile | Ile | Tyr |
|---|---|---|---|---|---|---|---|---|---|---|---|---|---|---|---|
| | | 115 | | | | | 120 | | | | | 125 | | | |

| Gln | Glu | Lys | Gln | Gly | Glu | Glu | Glu | Asp | Ala | Glu | Ile | Ile | Val | Lys | Ile |
|---|---|---|---|---|---|---|---|---|---|---|---|---|---|---|---|
| | 130 | | | | | 135 | | | | | 140 | | | | |

| Phe | Val | Glu | Phe | Ser | Ile | Ala | Ser | Glu | Thr | His | Lys | Ala | Ile | Gln | Ala |
|---|---|---|---|---|---|---|---|---|---|---|---|---|---|---|---|
| 145 | | | | | 150 | | | | | 155 | | | | | 160 |

| Leu | Asn | Gly | Arg | Trp | Phe | Ala | Gly | Arg | Lys | Trp | Trp | Leu | Lys | Cys | Thr |
|---|---|---|---|---|---|---|---|---|---|---|---|---|---|---|---|
| | | | | 165 | | | | | 170 | | | | | 175 | |

| Thr | Arg | Ser | Val | Leu | Ile | Thr | Val | Thr | Ser | Leu | Arg | Asp | Ser | Gly | Pro |
|---|---|---|---|---|---|---|---|---|---|---|---|---|---|---|---|
| | | | 180 | | | | | 185 | | | | | 190 | | |

| Ser | Pro | Arg | Thr | Cys | Thr | Cys | Ser | Leu | Phe | Pro | Leu | Gly | Phe | Ile | Val |
|---|---|---|---|---|---|---|---|---|---|---|---|---|---|---|---|
| | | 195 | | | | | 200 | | | | | 205 | | | |

| Ile | Gln | Trp | Cys | Pro | Arg | Gly | Gln | Ala | Arg | Ser | Ala | Gln | Pro | Ser | Leu |
|---|---|---|---|---|---|---|---|---|---|---|---|---|---|---|---|
| | 210 | | | | | 215 | | | | | 220 | | | | |

| Gln | Cys | Gly |
|---|---|---|
| 225 | | |

(2) INFORMATION FOR SEQ ID NO:2:

(i) SEQUENCE CHARACTERISTICS:
        (A) LENGTH: 895 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY:
        (B) CLONE: Consensus (xi) SEQUENCE DESCRIPTION: SEQ ID NO:2:

| | | | | | |
|---|---|---|---|---|---|
| TGCATCACTT | ACCACTAGTT | TTACATCGTC | GTGACTGGTG | CAAACCCTAG | GCTGTTACCC | 60 |
| ACACGTTAAG | TCGCCGTTTC | AGCACATTAG | TTGCCGGAGC | AGCGGTGCTG | GGTACCCTGG | 120 |
| GCACACCTGG | ACTGGTGTCC | CCAGCACTGA | CCCTGGCCCA | GCCCTGGGC | ACTTTGCCCC | 180 |
| AGGCTGTCAT | GGCTGCCCAG | GCACCTGGAG | TCATCACAGG | TGTGACCCCA | GCCCGTCCTC | 240 |
| CTATCCCGGT | CACCATCCCC | TCGGTGGGAG | TGGTGAACCC | CATCCTGGCC | AGCCCTCCAA | 300 |
| CGCTGGGTCT | CCTGGAGCCC | AAGAAGGAGA | AGGAAGAAGA | GGAGCTGTTT | CCCGAGTCAG | 360 |
| AGCGGCCAGA | GATGCTGAGC | GAGCAGGAGC | ACATGAGCAT | CTCGGGCAGT | AGCGCCCGAC | 420 |

```
ACATGGTGAT  GCAGAAGCTG  CTCCGCAAGC  AGGAGTCTAC  AGTGATGGTT  CTGCGCAACA        480

TGGTGGACCC  CAAGGACATC  GATGATGACC  TGGAAGGGGA  GGTGACAGAG  GAGTGTGGCA        540

AGTTCGGGGC  CGTGAACCGC  GTCATCATCT  ACCAAGAGAA  ACAAGGCGAG  GAGGAGGATG        600

CAGAAATCAT  TGTCAAGATC  TTTGTGGAGT  TTTCCATAGC  CTCTGAGACT  CATAAGGCCA        660

TCCAGGCCCT  CAATGGCCGC  TGGTTTGCTG  GCCGCAAGTG  GTGGCTGAAG  TGTACGACCA        720

GGAGCGTTTT  GATAACAGTG  ACCTCTCTGC  GTGACAGTGG  TCCCTCTCCC  CGGACTTGCA        780

CTTGTTCCTT  GTTTCCTCTG  GGTTTTATAG  TGATACAGTG  GTGTCCCCGG  GGCCAGGCGC        840

GCTCTGCCCA  GCCCAGCCTA  CAGTGCGGAT  AAAGGTGCGG  ATGCTGCTGG  CCCTG             895
```

( 2 ) INFORMATION FOR SEQ ID NO:3:

( i ) SEQUENCE CHARACTERISTICS:
        ( A ) LENGTH: 383 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 166694

( x i ) SEQUENCE DESCRIPTION: SEQ ID NO:3:

```
Met  Leu  Gly  Gly  Leu  Tyr  Gly  Asp  Leu  Pro  Pro  Thr  Asp  Asp  Glu
 1              5                        10                       15

Lys  Pro  Ser  Gly  Asn  Ser  Ser  Val  Trp  Ser  Arg  Ser  Thr  Lys  Met
              20                       25                       30

Ala  Pro  Pro  Thr  Leu  Arg  Lys  Pro  Ala  Phe  Ala  Pro  Pro  Gln  Thr
              35                       40                       45

Ile  Leu  Arg  Pro  Leu  Asn  Lys  Pro  Lys  Pro  Ile  Val  Ser  Ala  Pro  Tyr
         50                       55                       60

Lys  Pro  Pro  Pro  Asn  Ser  Ser  Gln  Ser  Val  Leu  Ile  Pro  Ala  Asn  Glu
 65                       70                       75                       80

Ser  Ala  Pro  Ser  His  Gln  Pro  Ala  Leu  Val  Gly  Val  Thr  Ser  Ser  Val
                   85                       90                       95

Ile  Glu  Glu  Tyr  Asp  Pro  Ala  Arg  Pro  Asn  Asp  Tyr  Glu  Glu  Tyr  Lys
                  100                      105                      110

Arg  Glu  Lys  Lys  Arg  Lys  Ala  Thr  Glu  Ala  Glu  Met  Lys  Arg  Glu  Met
                  115                      120                      125

Asp  Lys  Arg  Arg  Gln  Val  Tyr  Pro  Glu  Arg  Asp  Met  Arg  Glu  Arg  Glu
              130                      135                      140

Glu  Arg  Glu  Arg  Arg  Glu  Arg  Glu  Ile  Thr  Val  Ile  Leu  Ser  Val  Asp
145                      150                      155                      160

Ile  Ser  Gly  Glu  Glu  Arg  Gly  Arg  Asp  Pro  Ala  Arg  Val  Val  Glu
                       165                      170                      175

Val  Leu  Gly  Arg  Glu  Asp  Pro  Arg  Leu  Leu  Pro  Gly  Asn  Val  Asp  Gly
                   180                      185                      190

Phe  Ser  Ile  Gly  Lys  Ser  Lys  Pro  Ser  Gly  Leu  Gly  Val  Gly  Ala  Gly
              195                      200                      205

Gly  Gln  Met  Thr  Pro  Ala  Gln  Arg  Met  Met  Pro  Lys  Met  Gly  Trp  Lys
     210                      215                      220

Gln  Gly  Gln  Gly  Leu  Gly  Lys  Ser  Glu  Gln  Gly  Ile  Pro  Thr  Pro  Leu
225                      230                      235                      240

Met  Ala  Lys  Lys  Thr  Asp  Arg  Arg  Ala  Gly  Val  Ile  Val  Asn  Ala  Ser
```

|     | 245 |     |     |     | 250 |     |     |     | 255 |     |     |
| --- | --- | --- | --- | --- | --- | --- | --- | --- | --- | --- | --- |

Glu Asn Lys Ser Ser Ser Ala Glu Lys Lys Val Val Lys Ser Val Asn
              260                 265                 270

Ile Asn Gly Glu Pro Thr Arg Val Leu Leu Leu Arg Asn Met Val Gly
          275                 280                 285

Pro Gly Gln Val Asp Asp Glu Leu Glu Asp Glu Val Gly Gly Glu Cys
      290                 295                 300

Ala Lys Tyr Gly Thr Val Thr Arg Val Leu Ile Phe Glu Ile Thr Glu
305               310                 315                     320

Pro Asn Phe Pro Val His Glu Ala Val Arg Ile Phe Val Gln Phe Ser
              325                 330                 335

Arg Pro Glu Glu Thr Thr Lys Ala Leu Val Asp Leu Asp Gly Arg Tyr
          340                 345                 350

Phe Gly Gly Arg Thr Val Arg Ala Thr Phe Tyr Asp Glu Glu Lys Phe
          355                 360                 365

Ser Lys Asn Glu Leu Ala Pro Val Pro Gly Glu Ile Pro Gly Tyr
    370                 375                 380

( 2 ) INFORMATION FOR SEQ ID NO:4:

( i ) SEQUENCE CHARACTERISTICS:
        ( A ) LENGTH: 475 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 267188

( x i ) SEQUENCE DESCRIPTION: SEQ ID NO:4:

Met Ser Asp Phe Asp Glu Phe Glu Arg Gln Leu Asn Glu Asn Lys Gln
  1               5                  10                  15

Glu Arg Asp Lys Glu Asn Arg His Arg Lys Arg Ser His Ser Arg Ser
              20                  25                  30

Arg Ser Arg Asp Arg Lys Arg Arg Ser Arg Ser Arg Asp Arg Arg Asn
          35                  40                  45

Arg Asp Gln Arg Ser Ala Ser Arg Asp Arg Arg Arg Ser Lys Pro
      50                  55                  60

Leu Thr Arg Gly Ala Lys Glu Glu His Gly Gly Leu Ile Arg Ser Pro
 65                  70                  75                  80

Arg His Glu Lys Lys Lys Val Arg Lys Tyr Trp Asp Val Pro Pro
              85                  90                  95

Pro Gly Phe Glu His Ile Thr Pro Met Gln Tyr Lys Ala Met Gln Ala
              100                 105                 110

Ala Gly Gln Ile Pro Ala Thr Ala Leu Leu Pro Thr Met Thr Pro Asp
          115                 120                 125

Gly Leu Ala Val Thr Pro Thr Pro Val Pro Val Val Gly Ser Gln Met
    130                 135                 140

Thr Arg Gln Ala Arg Arg Leu Tyr Val Gly Asn Ile Pro Phe Gly Ile
145                 150                 155                 160

Thr Glu Glu Ala Met Met Asp Phe Phe Asn Ala Gln Met Arg Leu Gly
              165                 170                 175

Gly Leu Thr Gln Ala Pro Gly Asn Pro Val Leu Ala Val Gln Ile Asn
          180                 185                 190

Gln Asp Lys Asn Phe Ala Phe Leu Glu Phe Arg Ser Val Asp Glu Thr

```
                    1 9 5                              2 0 0                              2 0 5
Thr   Gln   Ala   Met   Ala   Phe   Asp   Gly   Ile   Ile   Phe   Gln   Gly   Gln   Ser   Leu
      2 1 0                              2 1 5                              2 2 0

Lys   Ile   Arg   Arg   Pro   His   Asp   Tyr   Gln   Pro   Leu   Pro   Gly   Met   Ser   Glu
2 2 5                              2 3 0                              2 3 5                        2 4 0

Asn   Pro   Ser   Val   Tyr   Val   Pro   Gly   Val   Val   Ser   Thr   Val   Val   Pro   Asp
                        2 4 5                              2 5 0                              2 5 5

Ser   Ala   His   Lys   Leu   Phe   Ile   Gly   Gly   Leu   Pro   Asn   Tyr   Leu   Asn   Asp
                  2 6 0                              2 6 5                              2 7 0

Asp   Gln   Val   Lys   Glu   Leu   Leu   Thr   Ser   Phe   Gly   Pro   Leu   Lys   Ala   Phe
                  2 7 5                              2 8 0                              2 8 5

Asn   Leu   Val   Lys   Asp   Ser   Ala   Thr   Gly   Leu   Ser   Lys   Gly   Tyr   Ala   Phe
      2 9 0                              2 9 5                              3 0 0

Cys   Glu   Tyr   Val   Asp   Ile   Asn   Val   Thr   Asp   Gln   Ala   Ile   Ala   Gly   Leu
3 0 5                              3 1 0                              3 1 5                        3 2 0

Asn   Gly   Met   Gln   Leu   Gly   Asp   Lys   Lys   Leu   Leu   Val   Gln   Arg   Ala   Ser
                        3 2 5                              3 3 0                              3 3 5

Val   Gly   Ala   Lys   Asn   Ala   Thr   Leu   Val   Ser   Pro   Pro   Ser   Thr   Ile   Asn
                  3 4 0                              3 4 5                              3 5 0

Gln   Thr   Pro   Val   Thr   Leu   Gln   Val   Pro   Gly   Leu   Met   Ser   Ser   Gln   Val
                  3 5 5                              3 6 0                              3 6 5

Gln   Met   Gly   Gly   His   Pro   Thr   Glu   Val   Leu   Cys   Leu   Met   Asn   Met   Val
      3 7 0                              3 7 5                              3 8 0

Leu   Pro   Glu   Glu   Leu   Leu   Asp   Asp   Glu   Glu   Tyr   Glu   Glu   Ile   Val   Glu
3 8 5                              3 9 0                              3 9 5                        4 0 0

Asp   Val   Arg   Asp   Glu   Cys   Ser   Lys   Tyr   Gly   Leu   Val   Lys   Ser   Ile   Glu
                        4 0 5                              4 1 0                              4 1 5

Ile   Pro   Arg   Pro   Val   Asp   Gly   Val   Glu   Val   Pro   Gly   Cys   Gly   Lys   Ile
                  4 2 0                              4 2 5                              4 3 0

Phe   Val   Glu   Phe   Thr   Ser   Val   Phe   Asp   Cys   Gln   Lys   Ala   Met   Gln   Gly
                  4 3 5                              4 4 0                              4 4 5

Leu   Thr   Gly   Arg   Lys   Phe   Ala   Asn   Arg   Val   Val   Val   Thr   Lys   Tyr   Cys
      4 5 0                              4 5 5                              4 6 0

Asp   Pro   Asp   Ser   Tyr   His   Arg   Arg   Asp   Phe   Trp
4 6 5                              4 7 0                              4 7 5
```

( 2 ) INFORMATION FOR SEQ ID NO:5:

( i ) SEQUENCE CHARACTERISTICS:
        ( A ) LENGTH: 416 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 627165

( x i ) SEQUENCE DESCRIPTION: SEQ ID NO:5:

```
Met   Gly   Tyr   Asp   Asp   Arg   Glu   Arg   Asp   Arg   Glu   Arg   Arg   Arg   His   Arg
1                             5                               1 0                              1 5

Ser   Arg   Ser   Arg   Asp   Arg   His   Arg   Glu   Arg   Ser   Arg   Asp   Arg   Arg   His
                  2 0                              2 5                              3 0

His   Arg   Asn   Ser   Arg   Arg   Lys   Pro   Ser   Leu   Tyr   Trp   Asp   Val   Pro   Pro
      3 5                              4 0                              4 5

Pro   Gly   Phe   Glu   His   Ile   Thr   Pro   Met   Gln   Tyr   Lys   Ala   Met   Gln   Ala
```

-continued

|  |  | 50 |  |  |  | 55 |  |  |  | 60 |  |  |  |
|---|---|---|---|---|---|---|---|---|---|---|---|---|---|
| Ser 65 | Gly | Gln | Ile | Pro | Ala 70 | Ser | Val | Val | Pro | Asp 75 | Thr | Pro | Gln | Thr | Ala 80 |
| Val | Pro | Val | Val | Gly 85 | Ser | Thr | Ile | Thr | Arg 90 | Gln | Ala | Arg | Arg | Leu 95 | Tyr |
| Val | Gly | Asn | Ile 100 | Pro | Phe | Gly | Val | Thr 105 | Glu | Glu | Glu | Met | Met 110 | Glu | Phe |
| Phe | Asn | Gln 115 | Gln | Met | His | Leu | Val 120 | Gly | Leu | Ala | Gln | Ala 125 | Ala | Gly | Ser |
| Pro | Val 130 | Leu | Ala | Cys | Gln | Ile 135 | Asn | Leu | Asp | Lys | Asn 140 | Phe | Ala | Phe | Leu |
| Glu 145 | Phe | Arg | Ser | Ile | Asp 150 | Glu | Thr | Thr | Gln | Ala 155 | Met | Ala | Phe | Asp | Gly 160 |
| Ile | Asn | Leu | Lys | Gly 165 | Gln | Ser | Leu | Lys | Ile 170 | Arg | Arg | Pro | His | Asp 175 | Tyr |
| Gln | Pro | Met | Pro 180 | Gly | Ile | Thr | Asp | Thr 185 | Pro | Ala | Ile | Lys | Pro 190 | Ala | Val |
| Val | Ser | Ser 195 | Gly | Val | Ile | Ser | Thr 200 | Val | Val | Pro | Asp | Ser 205 | Pro | His | Lys |
| Ile | Phe 210 | Ile | Gly | Gly | Leu | Pro 215 | Asn | Tyr | Leu | Asn | Asp 220 | Asp | Gln | Val | Lys |
| Glu 225 | Leu | Leu | Leu | Ser | Phe 230 | Gly | Lys | Leu | Arg | Ala 235 | Phe | Asn | Leu | Val | Lys 240 |
| Asp | Ala | Ala | Thr | Gly 245 | Leu | Ser | Lys | Gly | Tyr 250 | Ala | Phe | Cys | Glu | Tyr 255 | Val |
| Asp | Leu | Ser | Ile 260 | Thr | Asp | Gln | Ser | Ile 265 | Ala | Gly | Leu | Asn | Gly 270 | Met | Gln |
| Leu | Gly | Asp 275 | Lys | Lys | Leu | Ile | Val 280 | Gln | Arg | Ala | Ser | Val 285 | Gly | Ala | Lys |
| Asn | Ala 290 | Gln | Asn | Ala | Ala | Asn 295 | Thr | Thr | Gln | Ser | Val 300 | Met | Leu | Gln | Val |
| Pro 305 | Gly | Leu | Ser | Asn | Val 310 | Val | Thr | Ser | Gly | Pro 315 | Pro | Thr | Glu | Val | Leu 320 |
| Cys | Leu | Leu | Asn | Met 325 | Val | Thr | Pro | Asp | Glu 330 | Leu | Arg | Asp | Glu | Glu 335 | Glu |
| Tyr | Glu | Asp | Ile 340 | Leu | Glu | Asp | Ile | Lys 345 | Glu | Glu | Cys | Thr | Lys 350 | Tyr | Gly |
| Val | Val | Arg 355 | Ser | Val | Glu | Ile | Pro 360 | Arg | Pro | Ile | Glu | Gly 365 | Val | Glu | Val |
| Pro | Gly 370 | Cys | Gly | Lys | Val | Phe 375 | Val | Glu | Phe | Asn | Ser 380 | Val | Leu | Asp | Cys |
| Gln 385 | Lys | Ala | Gln | Gln | Ala 390 | Leu | Thr | Gly | Arg | Lys 395 | Phe | Ser | Asp | Arg | Val 400 |
| Val | Val | Thr | Ser | Tyr 405 | Phe | Asp | Pro | Asp | Lys 410 | Tyr | His | Arg | Arg | Glu 415 | Phe |